(12) United States Patent
Prendergast

(10) Patent No.: US 8,076,311 B2
(45) Date of Patent: Dec. 13, 2011

(54) COMPOSITIONS AND METHODS FOR MODULATING THE IMMUNE SYSTEM

(76) Inventor: Patrick T. Prendergast, New South Wales (AU)

(*) Notice: Subject to any disclaimer, the term of this patent is extended or adjusted under 35 U.S.C. 154(b) by 189 days.

(21) Appl. No.: 12/227,256

(22) PCT Filed: May 11, 2007

(86) PCT No.: PCT/EP2007/054605
§ 371 (c)(1),
(2), (4) Date: Dec. 8, 2008

(87) PCT Pub. No.: WO2007/131973
PCT Pub. Date: Nov. 22, 2007

(65) Prior Publication Data
US 2009/0156546 A1 Jun. 18, 2009

Related U.S. Application Data

(60) Provisional application No. 60/810,961, filed on Jun. 5, 2006.

(30) Foreign Application Priority Data

May 11, 2006 (GB) .................................. 0609478.3
May 12, 2006 (GB) .................................. 0609406.4

(51) Int. Cl.
*A01N 43/04* (2006.01)
*A61K 31/70* (2006.01)

(52) U.S. Cl. .............. 514/46; 514/43; 514/45; 514/47
(58) Field of Classification Search .................. None
See application file for complete search history.

(56) References Cited

U.S. PATENT DOCUMENTS

2003/0191137 A1* 10/2003 Kim et al. ............... 514/255.05

FOREIGN PATENT DOCUMENTS

| CN | 1625399 A | 6/2005 |
| EP | 0 462 621 | 12/1991 |
| WO | WO 01/64215 | 9/2001 |
| WO | WO 03/066058 | 8/2003 |

OTHER PUBLICATIONS

Chi et al. Carcinogenesis (1998), vol. 19, pp. 2133-2138.*
Ruggeri et al. Clinical Cancer Research (2002), vol. 8, pp. 267-274.*
Spivak The Lancet (2000), vol. 355, pp. 1707-1712.*
Kim, et al., "In Vivo Radioprotective Effects of Oltipraz in γ-Irradiated Mice", Biochemical Pharmacology, vol. 55, pp. 1585-1590, 1998.

* cited by examiner

*Primary Examiner* — Patrick Lewis
(74) *Attorney, Agent, or Firm* — Drinker Biddle & Reath LLP

(57) ABSTRACT

The present invention provides methods and compositions for the prophylaxis of blood cell disorders such as neutropenia, thrombocytopenia, lymphocytopenia, and anaemia. The invention provides methods wherein compositions comprising at least one cytokinin compound are administered either therapeutically or prophylactically. The invention further has utility in methods of DNA repair.

18 Claims, 2 Drawing Sheets

COMPOSITIONS AND METHODS FOR MODULATING THE IMMUNE SYSTEM

FIELD OF THE INVENTION

Figure 1:
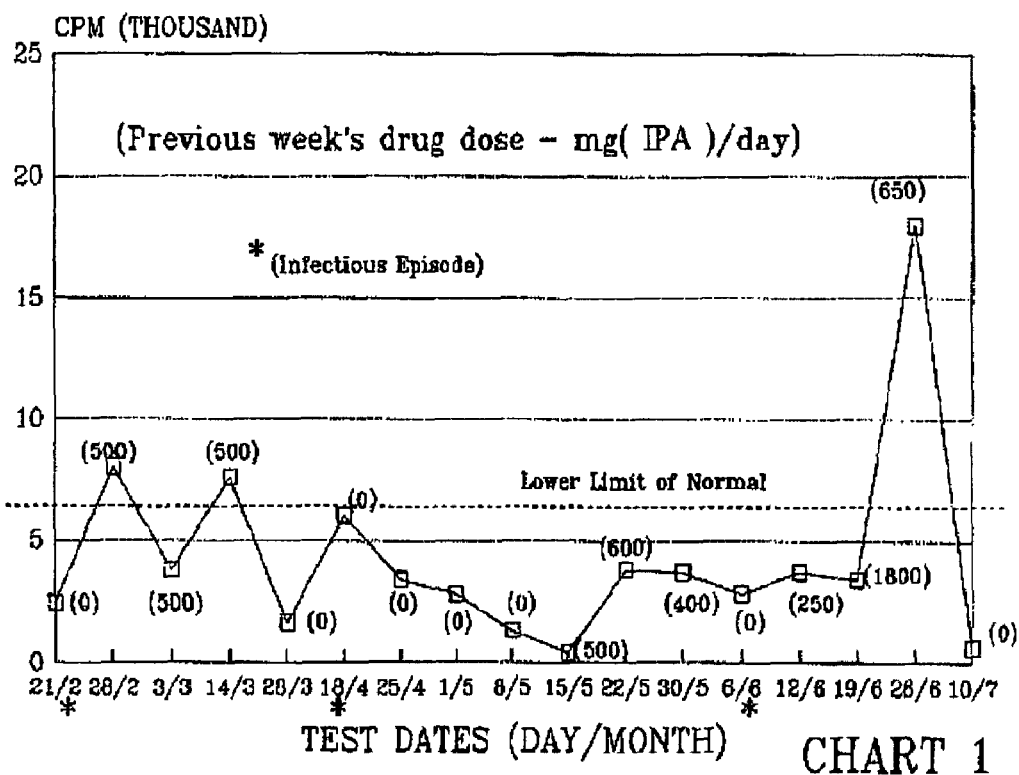

The present invention relates to methods for stimulating the production of cells of white blood cells. In particular, the present invention provides compositions and methods for the enhancement of blood cell production. Specifically, the use of the compounds, compositions and methods of the invention can be used to ameliorate or treat conditions such as neutropenia, thrombocytopenia, anaemia and other blood cell deficiencies or other exemplified conditions such as reactive oxidative stress which result from or are caused by gamma x-ray or proton radiation exposure.

BACKGROUND TO THE INVENTION

The suppression or dysregulation of the immune system can be a component of many pathological diseases or conditions. In particular, immune dysregulation can result in the onset and progression of disease. Where onset of disease occurs, the dysregulation of the immune system means that an individual is compromised against mounting a full immune response against a particular disease or pathogenic condition.

Acute Radiation Syndrome (ARS) results from the exposure of an individual to a high level of radiation. ARS is a life threatening condition, primarily due to the depletion in the blood cell count. High levels of radiation inhibits production of blood cells by the bone marrow. Such blood cells include; white blood cells, neutrophils, platelets and factors required for blood clotting. Severe depletion of these blood components results in conditions such as neutropenia, where a low neutrophil count is present and thrombocytopenia where there is a low platelet count.

Although the bone marrow can functionally revert to produce blood cell components at the level produced prior to radiation exposure, this reversion can take up to 3 months. In the interim, the immune system is severely compromised due to the depletion in cell numbers, and in particular due to a depleted neutrophil count.

With the possibility of a terrorist attack which would include, in some form, a radioactive element, there is the need for viable treatments to ARS which are cost effective and which are easy to produce and administer, and which have previous human use for other indications.

Chemotherapy can also cause damage to bone marrow and accordingly result in a decrease in neutrophil and platelet count. Again, the use of compounds which could be administered to reduce the side effects of chemotherapy on bone marrow cell production would be highly desirable.

The inventor of the present invention has surprisingly identified two groups of compounds which have been unexpectedly shown to mediate, either on their own, or in combination with other compounds, a protective effect against blood cell depletion. Preventing blood cell depletion can mediate the remission of neutropenia, thrombocytopenia and anaemia, and can also stimulate an enhancement of B cell and T cell function, following such function being compromised due to exposure of a subject to radiation.

The compounds identified by the inventor are non steroidal compounds, which have been unexpectedly shown to have utility in the treatment and/or amelioration of one or more condition which can be attributed to a deficiency or dysregulation in blood cell number, and in particular of the function of the immune system. This dysregulation is particularly characterised by a reduction in a reduction in a number of cells, such as lymphocytes which have a role or function in mediating immunity. As such, the compounds of the present invention have utility in methods for the treatment of immunosuppressive conditions mediated by exposure to radiation, and in particular to blood cell deficiencies such as neutropenia and thrombocytopenia.

SUMMARY OF THE INVENTION

According to a first aspect of the present invention there is provided a method for the treatment and/or prophylaxis of blood cell depletion, the method comprising:
providing a therapeutically effective or prophylactically effective amount of oltipraz or a derivative, analogue, metabolite, prodrug or pharmaceutically acceptable salt thereof, and
administering the same to a subject in need of such treatment.

In certain embodiments, the blood cell depletion results in immune dysregulation. In certain further embodiments, the blood cell depletion results in a condition selected from, but not limited to; neutropenia, thrombocytopenia, lymphocytopenia, and anaemia.

As herein defined, neutrotopenia is a condition characterised by a decrease in the number of neutrophils. Lymphocytopenia is a condition characterised by a decrease in the number of lymphocytes. Thrombocytopenia is a condition characterised by a decrease in the number of platelets.

In certain embodiments, the neutropenia is selected from the group consisting of, but not limited to; postinfectious neutropenia, autoimmune neutropenia, chronic idiopathic neutropenia or a neutropenia resulting from, or potentially resulting from, chemotherapy for use in the treatment of a cancerous condition, chemotherapy for the treatment of an autoimmune disease, an antiviral therapy, direct radiation exposure, secondary radiation exposure through environmental contamination, tissue or solid organ allograft or xenograft rejection or immune suppression therapy in tissue or solid organ transplantation or aging or immunesenescence.

In certain further embodiments, the condition is reactive oxidative stress, for example, reactive oxidative stress which may result from, or which may be caused by exposure of a subject to gamma, x-ray or proton radiation exposure.

The structure of oltipraz is shown in Formula I:

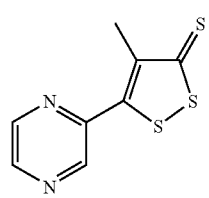

Formula I

In certain further embodiments, the metabolite of oltipraz (also known as the dithiolethione oltipraz (OPZ)) is metabolite 3 (also known as M3). Oltipraz undergoes metabolism by molecular rearrangement to yield M3, a pyrrolopyrazine derivative.

In certain further embodiments, oltipraz or a derivative, analogue, metabolite or prodrug thereof is formulated along with carboxymethyl cellulose (CMC) to form a combined medicament. Carboxymethyl cellulose is a cellulose derivative with carboxymethyl groups bound to some of the hydroxyl groups of the glucopyranose monomers that make up the cellulose backbone.

The inventor has surprisingly identified that formulating oltipraz along with carboxymethyl cellulose results in a marked reduction in toxicity. Specifically, and without wishing to be bound by theory, the inventor has identified that when formulated this way, oltipraz is safe for administration to a subject in an amount of 2000 mg/kg. The inventor has identified that oltipraz, when administered individually, is expected to cause toxicity in the liver at levels of 50 to 100 mg/kg. The inventor has identified that when formulated with carboxymethyl cellulose, oltipraz is not absorbed into the bloodstream, but rather lines the digestive tract, this serving to protect against damage such as gastrointestinal damage.

In a further aspect of the present invention there is provided a pharmaceutical composition for use in the treatment of blood cell depletion, the composition comprising oltipraz or a derivative, analogue, metabolite, prodrug or pharmaceutically acceptable salt thereof, along with a pharmaceutically acceptable diluent and/or carrier.

Typically the pharmaceutically acceptable diluent or carrier will be selected depending upon the intended route of administration of the pharmaceutical composition.

In certain embodiments, the composition comprises the oltipraz derivative M3 (metabolite 3).

In certain embodiments, the pharmaceutical composition further comprises carboxymethyl cellulose.

A further aspect of the invention provides for the use of oltipraz or a derivative, analogue, metabolite, prodrug or pharmaceutically acceptable salt thereof in the preparation of a medicament for the treatment of blood cell disorder.

In certain embodiments, the blood cell disorder is selected from the group consisting of, but not limited to; neutropenia, thrombocytopenia, lymphocytopenia, and anaemia.

In certain embodiments, the derivative of oltipraz is M3 (metabolite 3). In certain further embodiments, the composition further comprises carboxymethyl cellulose.

A still further aspect of the present invention provides a kit comprising oltipraz or a derivative, analogue, metabolite, prodrug or pharmaceutically acceptable salt thereof for use in preventing blood cell depletion.

Without wishing to be bound by theory, the inventor predicts, that the mode of action is derived from oltipraz or a derivative or analogue thereof chelating with, or forming a complex with, one or more divalent or trivalent radioactive metal ions, whereby the divalent or trivalent radioactive ions in the subject's cells or tissues are redistributed or sequestered such that the ions are limited in their capacity to participate in unwanted tissue destruction.

In certain embodiments, the divalent or trivalent metal ions are selected from the group comprising, but not limited to: Fe, Cu, Ni, Ca, Mg, Mn, Cd, Pb, Al, Hg, Co, I, Se, Cs, U, Pa, Th, Ra, Ce, and Zn.

According to a further aspect of the present invention there is provided a method for the treatment and/or prophylaxis of blood cell depletion, the method comprising:
providing a therapeutically effective or prophylactically effective amount of at least one cytokinin compound, and
administering the same to a subject in need of such treatment.

In certain embodiments, the blood cell depletion results in immune dysregulation. In certain further embodiments, the blood cell depletion results in a condition selected from, but not limited to; neutropenia, thrombocytopenia, lymphocytopenia, and anaemia.

As herein defined, neutrotopenia is a condition characterised by a decrease in the number of neutrophils. Lymphocytopenia is a condition characterised by a decrease in the number of lymphocytes. Thrombocytopenia is a condition characterised by a decrease in the number of platelets.

In certain embodiments, the neutropenia is selected from the group consisting of, but not limited to; postinfectious neutropenia, autoimmune neutropenia, chronic idiopathic neutropenia or a neutropenia resulting from, or potentially resulting from, chemotherapy for use in the treatment of a cancerous condition, chemotherapy for the treatment of an autoimmune disease, an antiviral therapy, direct radiation exposure, secondary radiation exposure through environmental contamination, tissue or solid organ allograft or xenograft rejection or immune suppression therapy in tissue or solid organ transplantation or aging or immunesenescence.

In certain further embodiments, the condition is reactive oxidative stress, for example, reactive oxidative stress which may result from, or which may be caused by exposure of a subject to gamma, x-ray or proton radiation exposure.

In certain embodiments, the cytokinin compound is $N^6$ isopentenyl adenosine or an analogue, derivative, metabolite, prodrug or pharmaceutically acceptable salt thereof.

In a further embodiment, the method further comprises the step of administering to the subject a therapeutically effective amount of oltipraz or a derivative, analogue, metabolite, prodrug or pharmaceutically acceptable salt thereof.

Examples of $N^6$ isopentenyl adenosine or an analogue, derivative, metabolite, prodrug or pharmaceutically acceptable salt thereof are shown below, said compounds being described hereinafter.

In certain embodiments, $N^6$ isopentenyl adenosine compounds according to Formula 2 are provided:

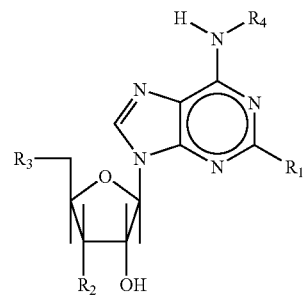

Formula II wherein:
R1=H, R2=CH3, R3=CH3, and R4=H, or R1=H or CH3S and R4 is as follows:

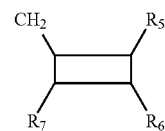

and R5=CH3, Cl, OH or a monophosphate group, R6=CH3, CH2OH or Cl, and R7=H or Br, or R1=H and R4 is as follows:

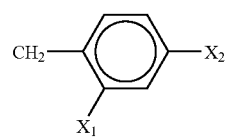

and X1 and X2 are independently selected from H, methyl, ethyl, hydroxyl, a halogen and carboxyl or R4 is as follows:

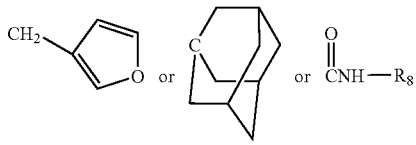

and wherein R8 is as follows:

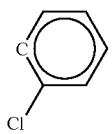

or (CH$_2$)$_7$CH$_3$;

and R2=OH and R3=OH, monophosphate, diphosphate or triphosphate group, or R2 and R3 are linked to form a 3', 5'-cyclic monophosphate derivative, or a physiologically acceptable salt of any such compound.

Formula II is used herein to refer to all of such compounds and salts.

This aspect of the invention further extends to further N$^6$ isopentenyl adenosine compounds as described below. These compounds are listed hereinafter as compounds Ia through to Iu, wherein said compounds define the constituents of R1, R2, R3 and R4 of Formula II. The compounds are as follows:

Compound Ia wherein: R1=H, R2=OH, R3=OH and R4 is as follows:

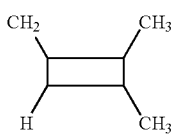

This compound being known as N6-(Δ2-isopentenyl) adenosine.

Compound Ib wherein: R1=H, R2=OH, R3=monophosphate and R4 is as follows:

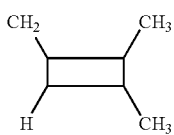

This compound being known as N6-(Δ2-isopentenyl) adenosine-5'-monosphosphate.

Compound Ic wherein: R1=H, R2 and R3 are linked to form a 3', 5'-cyclic monophosphate derivative, and R4 is as follows:

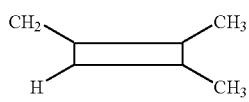

This compound being known as N6-(Δ2-isopentenyl) adenosine-5'-cyclic monosphosphate.

Compound Id wherein: R1=H, R2=OH, R3=OH and R4=CH2C6H6, the compound being known as N6-benzyladenosine.

Compound Ie wherein: R1=H, R2=OH, R3=monophosphate, and R4=CH2C6H6. The compound being known as N6-benzyladenosine-5'-monophosphate.

Compound If wherein: R1=H, R2 and R3 are linked to form a 3', 5'-cyclic monophosphate derivative and R4=CH2C6H6. Wherein the compound is known as N6-benzyladenosine-3', 5'cyclic monophosphate.

Compound Ig, wherein: R1=H, R2=OH, R3=OH, and R4 is as follows:

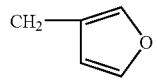

Wherein the compound is known as Furfuryladenosine.

Compound Ih which is N6-furfuryladenosine-5'monophosphate. Compound Ii which is N6-furfuryladenosine-3', 5'-cyclic monophosphate. Compound Ij which is N-(purin-6-ylcarbamoyl)-o-chloroaniline ribonucleoside. Compound Ik which is N-(purin-6-ylcarbamoyl)-o-chloroaniline ribonucleoside-5'monophosphate. Compound Il which is N6-adamantyladenosine. Compound Im which is N6-adamantyladenosine-5'-monophosphate. Compound In which is N-(purin-6-ylcarbamoyl)-n-octylamine ribonucleoside. Compound Io which is N-(purin-6-ylcarbamoyl)-n-octylamine ribonucleoside-5'-monophosphate. Compound Ip which is N-(purin-6-ylcarbamoyl)-n-octylamine ribonucleoside-3', 5'-cyclic monophosphate, Compound Iq which is N6-(Δ2-isopentyl)-2-methylioadenosine. Compound Ir which is N6-(4-hydroxy-3-methyl-trans-2-butenyl)-adenosine. Compound Is which is N6-(3-chloro-trans-butenyl) adenosine. Compound It which is N6-(3-chloro-cis-2-butenyl) adenosine. Compound Iu wherein: R1=H, R2=CH3, R3=CH3 and R4=H.

The present invention further extends to one or more metabolites of the compounds of Formula II. For example, preferred metabolites include: n6-(Δ2-isopentenyl) adenine, 6-N-(3-methyl-3-hydroxybutylamino) purine, adenine, hypoxathine, uric acid and methylated xanthines.

In certain further embodiments, N$^6$ isopentenyl adenosine or a derivative, analogue, metabolite or prodrug thereof is formulated along with carboxymethyl cellulose (CMC) to form a combined medicament. Carboxymethyl cellulose is a cellulose derivative with carboxymethyl groups bound to some of the hydroxyl groups of the glucopyranose monomers that make up the cellulose backbone.

The inventor has surprisingly identified that formulating N$^6$ isopentenyl adenosine along with carboxymethyl cellulose results in a marked reduction in toxicity. Specifically, and without wishing to be bound by theory, the inventor has identified that when formulated this way, N$^6$ isopentenyl adenosine is safe for administration to a subject in an amount of 2000 mg/kg. The inventor has identified that N$^6$ isopentenyl adenosine, when administered individually, is expected to cause toxicity in the liver at levels of 50 to 100 mg/kg. The inventor has identified that when formulated with carboxymethyl cellulose, $N^6$ isopentenyl adenosine is not absorbed into the bloodstream, but rather lines the digestive tract, this serving to protect against damage such as gastrointestinal damage.

In a further aspect of the present invention there is provided a pharmaceutical composition for use in the treatment of blood cell depletion, the composition comprising $N^6$ isopentenyl adenosine or a derivative, analogue, metabolite, prodrug or pharmaceutically acceptable salt thereof, along with a pharmaceutically acceptable diluent and/or carrier.

Typically the pharmaceutically acceptable diluent or carrier will be selected depending upon the intended route of administration of the pharmaceutical composition.

In certain embodiments, the pharmaceutical composition further comprises carboxymethyl cellulose.

A further aspect of the invention provides for the use of $N^6$ isopentenyl adenosine or a derivative, analogue, metabolite, prodrug or pharmaceutically acceptable salt thereof in the preparation of a medicament for the treatment of blood cell disorder.

In certain embodiments the $N^6$ isopentenyl adenosine is a compound according to Formula II.

In certain embodiments, the blood cell disorder is selected from the group consisting of, but not limited to; neutropenia, thrombocytopenia, lymphocytopenia, and anaemia.

A still further aspect of the present invention provides a kit comprising $N^6$ isopentenyl adenosine or a derivative, analogue, metabolite, prodrug or pharmaceutically acceptable salt thereof for use in preventing blood cell depletion.

In certain embodiments the $N^6$ isopentenyl adenosine is a compound according to Formula II.

In certain further embodiments, the cytokinin compound is $N^6$ benzyl adenosine or an analogue, derivative, metabolite, prodrug or pharmaceutically acceptable salt thereof.

Examples of $N^6$ benzyl adenosine or an analogue, derivative, metabolite, prodrug or pharmaceutically acceptable salt thereof are shown below, said compounds being described hereinafter.

In certain further embodiments, the $N^6$ benzyl adenosine is N6-Benzyl-adenosine-5'monophosphate, which is shown below as a compound having Formula III:

Formula III

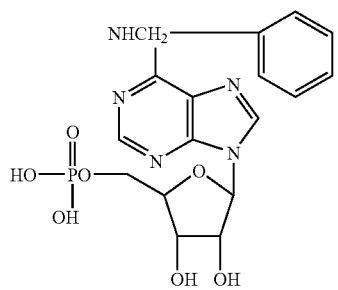

In certain further embodiments, the $N^6$ benzyl adenosine is (N6-Benzyl)Adenyl-p-(N6-Benzyl)Adenyl-p-(N6-Benzyl) Adenosine, which is shown below as a compound having Formula IV:

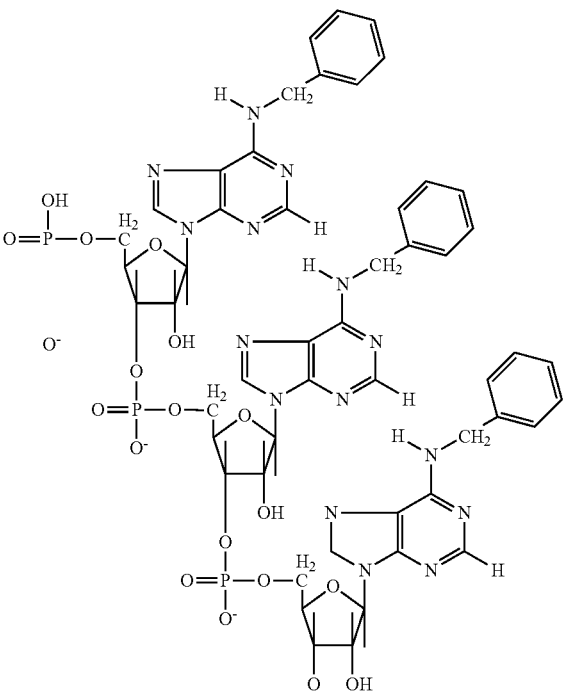

In certain further aspects, the present invention further extends to the following compounds:

ADT, having the general structure:

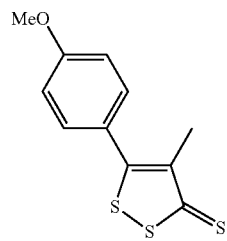

ADO, having the general structure:

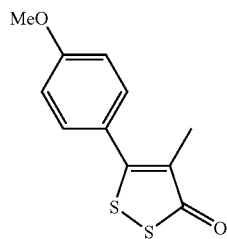

1,2-Dithiole 3-thione having the structure:

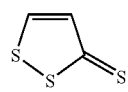

Lipoamide (1,2-dithiolane), having the structure:

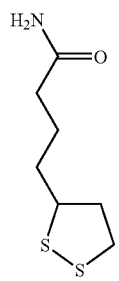

1,3-dithiole 2-thione having the structure:

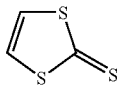

[1,2]Dithiolo[4,3-c]-1,2-dithiole-3,6-dithione having the structure:

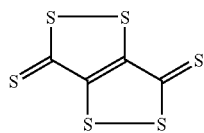

Malotilate having the general structure:

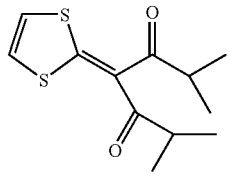

1,2-Dithiolane, class 1, having the general structure:

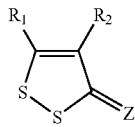

1,2-Dithiole, class 2, having the general structure:

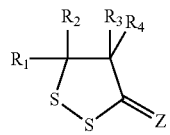

1,3-Dithiole, class 3, having the general structure:

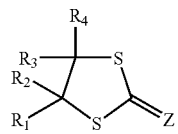

1,3-Dithioloane, class 4, having the general structure:

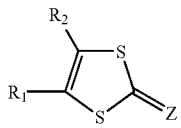

wherein Z=S,O,NR,R2,CR2 and Z can have the designations optionally and independently for all the classes. R in this case includes, H, alkyl (C1-C5), alkoxy (C1-C5), alkoxycarbononyl (C1-C5). R2 can form spiro rings about the ring carbon atom.

For the thiolane classes, the ring carbon atoms can be doubly substituted. R1-R4 are the main ring substituents for all classes and in order to cover a wide variety of substituents, should include optionally and independently H, alkyl, aryl, heterocyclic, halogen, alkoxycarbonyl (C1-C5) or carboxyl.

R1, R2 or R3, R4 can form a spiro ring around the carbon atom to which they are attached or they can form fused or bridged rings to adjacent carbons atoms. The following definitions cover the majority of compounds.

Alkyl is defined herein as C1-C10 linear or branched chain, saturated or unsaturated which can optionally be singly or multiply substituted by halogen, alkyl (C1-C5), hydroxyl, alkoxy (C1-C5), alkoxycarbonyl, (C1-C5), carboxyl, amido, alkyl amido (C1-C5), amino, mono and dialkyl amino (C1-C5), alkyl carbamoyl (C1-C5) thiol, alkythio (C1-C5) or benzenoid aryl.

Aryl is herein defined as any optionally singly or multiply substituted benzenoid group (C6-C14).

Heterocyclic radical means any 4, 5 or 6 membered, optionally hetercyclic ring, saturated or unsaturated, containing 1-3 ring atoms of which N, O or S, the remaining atoms being carbon.

Substituents on the aryl or heterocyclic radical include: halogen, alkyl $(C_1-C_5)$, hydroxyl, alkoxy $(C_1-C_5)$, alkoxycarbonyl, $(C_1-C_5)$, carboxyl, amido, alkyl amido $(C_1-C_5)$, amino, mono and dialkyl amino $(C_1-C_5)$, alkyl carbamoyl $(C_1-C_5)$, thiol, alkyl thio $(C_1-C_5)$ or benzenoid aryl, cyano, nitro, halo alkyls, alklsulfonyl $(C_1-C_5)$, sulfonate. Two of such substituents can be part of a fused ring, which can be either saturated, or unsaturated, heterocyclic or carbo cyclic.

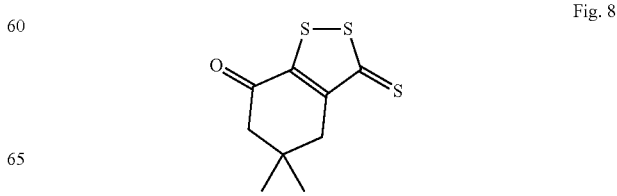

Fig. 8

-continued

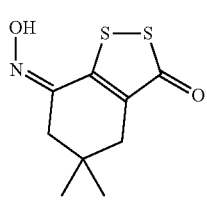

Fig. 9

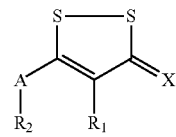

Fig. 10

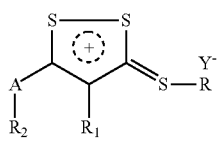

Fig. 11 in which
X is chosen from
=S
=O
=N—OH
=N—R$_5$
R$_5$, being a C$_1$-C$_6$ alkyl or an aryl group,
=N—NH—CO—NH$_2$ and
=N—NH—CS—NH$_2$ and

Z and Z' being electron-attracting groups such as ester or cyano groups.

A is chosen from a >C=N—OH group, a group of formula >C=N—OR$_3$ (where R$_3$ is chosen from hydroxyl, amino, chloro and C$_1$-C$_4$, alkoxy groups, an aryl (C$_1$-C$_6$ alkyl) group, a (C$_1$-C$_6$ alkyl) Carbonyl group and an aryl (C$_1$-C$_6$ alkyl) carbonyl group).

A may also be chosen from a >C=O group, a >C=N—R$_4$ group, R$_4$ being a C$_1$-C$_6$ alkyl group or an aryl group, and a CHOH group.

R$_1$ and R$_2$ are chosen, independently of one another, from hydrogen, a halogen, a nitro group, a nitroso group, a thiocyano group, a C$_1$-C$_6$ alkyl group, a C$_2$-C$_6$ alkenyl group, an aryl group, aryl (C$_1$-C$_6$ alkyl) group, an aryl (C$_2$-C$_6$ alkenyl) group, a carboxyl group, a (C$_1$-C$_6$ alkyl) carbonyl group, an arylcarbonyl group, a (C$_1$-C$_6$ alkoxy) carbonyl group, a (C$_1$-C$_6$ alkoxy) carbonyl (C$_1$-C$_6$ alkyl) group, a C$_1$-C$_6$ alkoxy group, a trifluoromethyl group, an amino group, a di (C$_1$-C$_6$ alkyl) amino (C$_1$-C$_6$ alkyl), an acylamino group of formula —NHCOC$_n$H$_{2n+1}$ with n from 0 to 6, a group —NH—CSC$_n$H$_{2n+1}$ with n from 0 to 6, a terpenyl group, a cyano group, a C$_2$-C$_6$ alkynyl group, a C$_2$-C$_6$ alkynyl group substituted with a C$_1$-C$_6$ alkyl or an aryl group, a hydroxy (C$_1$-C$_6$ alkyl) group, a (C$_1$-C$_6$ acyl) oxy (C$_1$-C$_6$ alkyl) group, a (C$_1$-C$_6$ alkyl) thio group and an arylthio group;
or alternatively R$_1$ and R$_2$ together form a mono- or polycyclic C$_2$-C$_{20}$ alkylene group optionally comprising one or more hetero atoms, with the exception of the 2,2dimethyltrimethylene group, or a C$_3$-C$_{12}$ cycloalkylene group.

R is chosen from a C$_1$-C$_6$, alkyl group, and their pharmaceutically acceptable salts.

In the foregoing definition, aryl group or aryl fraction of an arylalkyl group denotes an aromatic carbon-based group such as a phenyl or naphthyl group or an aromatic heterocyclic group such as a thienyl of furyl group, it being possible for these groups to bear one or more substituents chosen from a halogen atom, a C$_1$-C$_4$ alkyl group, a C$_1$-C$_4$ alkoxy group, a trifluoromethyl group, a nitro group and a hydroxyl group, Oximes of 1,2-dithiole-3-thione derivatives such as a shown in FIGS. 12, 13 & 14

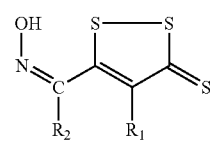

FIG. 12

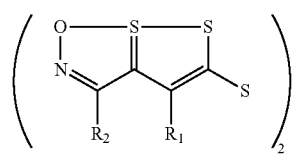

FIG. 13

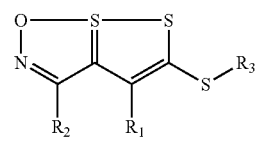

FIG. 14

Additionally Aldehydes or Ketones of previously identified compounds are incorporated such as shown in FIG. 15

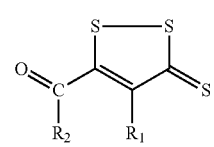

FIG. 15 one or more of the following compounds according to an embodiment wherein A (FIGS. 10, 11) is a group C=N—OR'$_3$ where R$_3$ is an optionally substituted C$_1$-C$_6$ alkyl group, in particular substituted with one or more groups chosen from hydroxyl, amino, chloro, bromo, fluro, iodo and C$_1$-C$_4$ alkoxy groups, or an aryl (C$_1$-C$_6$ alkyl) group, that is to say compounds of formula

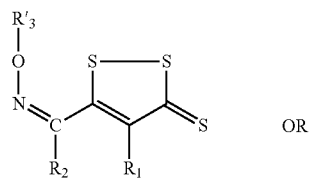

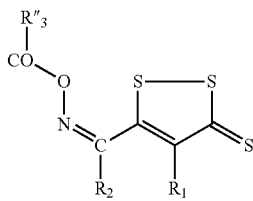

in which R3 has the meaning given above one or more of the following compounds as described in an embodiment (FIGS. 10 & 11) in which A is a group C=N—O—CO—R″$_3$, R″$_3$ being chosen from a hydrogen atom, an optionally substituted C$_1$-C$_6$ alkyl group, an aryl group and an aryl (C$_1$-C$_6$ alkyl) group, that is to say compounds of formula

FIG. 19

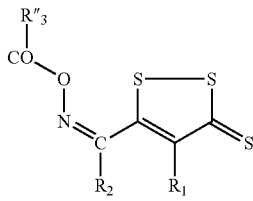

in which R″$_3$ being chosen from a hydrogen atom, an optionally substituted C$_1$-C$_6$ alkyl group, an aryl group.

Another group of compounds is formed by the compounds of embodiment (FIGS. 10 & 11) in which A is a CH—OH group, that is to say the compounds of formula

FIG. 20

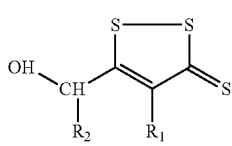

Another group of compounds is formed by the compounds of embodiment (FIGS. 10 & 11) in which A is a group C=N—R, R being a C$_1$-C$_6$ alkyl or an aryl group, that is to say compounds of formula

FIG. 21

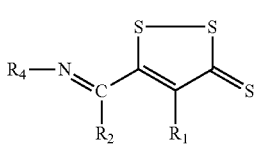

Another group of compounds include compounds of embodiment (FIGS. 10 & 11) in which A is a C=O group and X is an oxygen atom, that is to say compounds of formula:

FIG. 22

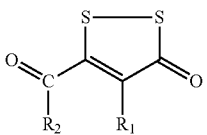

in which

R$_1$ is chosen from hydrogen, a halogen, a nitro group, a nitroso group, a thiocyano group, a C$_1$-C$_6$ alkyl group, a C$_2$-C$_6$ alkenyl group, an aryl group, an aryl (C$_1$-C$_6$ alkyl) group, an aryl (C$_2$-C$_6$ alkenyl) group, a carboxyl group, a (C$_1$-C$_6$ alkyl) carbonyl group, an arylcarbonyl group, a (C$_1$-C$_6$ alkoxy) carbonyl group, a (C$_1$-C$_6$ alkoxy) carbonyl (C$_1$-C$_6$ alkyl) group a (C$_1$-C$_6$ alkoxy group, a trifluoromethyl group, an amino group, a di (C$_1$-C$_6$ alkyl) amino (C$_1$-C$_6$ alkyl) group, an acylamino group of formula —NHCOC$_n$H$_{2n+1}$ with n from 0 to 6, a group —NH—CSC$_n$H$_{2n+1}$ with n from 0 to 6, a terpenyl group, a cyano group, a C$_1$-C$_6$ alkynyl group, a C$_2$-C$_6$ alkynyl group substituted with a C$_1$-C$_6$ alkyl or an aryl group, a hydroxy (C$_1$-C$_6$ alkyl) group, a (C$_1$-C$_6$ acyl)-oxy(C$_1$-C$_6$ alkyl) group, a C$_1$-C$_6$ alkyl)thio group and an arylthio group.

R$_2$ is chosen from a nitro group, a nitroso group, a thiocyano group, a C$_1$-C$_6$ alkyl group, a C$_2$-C$_6$ alkenyl group, an aryl group, an aryl (C$_1$-C$_6$ alkyl) group, an aryl (C$_1$-C$_6$ alkenyl) group, a carboxyl group, a(C$_1$-C$_6$ alkyl)carbonyl group, an arylcarbonyl group, a (C$_1$-C$_6$ alkoxy)carbonyl group, a (C$_1$-C$_6$ alkyl) group, a trifluoromethyl group, a di(C$_1$-C$_6$ alkyl) amino(C$_1$-C$_6$ alkyl) group, an acylamino group of formula —NHCOC$_n$H$_{2n+1}$ with n from 0 to 6, a group —NH—CSC$_n$H$_{2n+1}$ with n from 0 to 6, a terpenyl group, a cyano group, a C$_2$-C$_6$ alkynl group, a C$_2$-C$_6$ alkynyl group substituted with a C$_1$-C$_6$ alkyl or an aryl group, a hydroxy (C$_1$-C$_6$ alkyl) group, a C$_1$-C$_6$ acyl-oxy(C$_1$-C$_6$ alkyl) group, a (C$_1$-C$_6$ alkyl)thio group and an arylthio group;

or alternatively R$_1$ and R$_2$ together form a mono- or polycyclic C$_2$-C$_{20}$ alkylene group optionally comprising one or more hetero atoms, one or more of the following compounds of formula shown in FIG. 23

FIG. 23

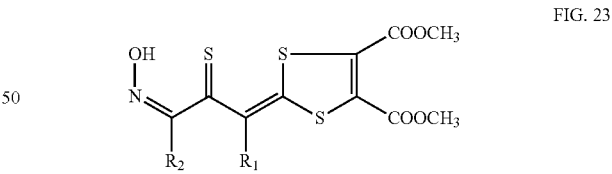

R$_1$ and R$_2$ are chosen, independently of one another, from hydrogen, a halogen, a nitro group, a nitroso group, a thiocyano group, a C$_1$-C$_6$ alkyl group, a C$_2$-C$_6$ alkenyl group, an aryl group, aryl(C$_1$-C$_6$ alkyl) group, an aryl (C$_2$-C$_6$ alkenyl) group, a carboxyl group, a (C$_1$-C$_6$ alkyl)carbonyl group, an arylcarbonyl group, a (C$_1$-C$_6$ alkoxy)carbonyl group, a (C$_1$-C$_6$ alkoxy)carbonyl (C$_1$-C$_6$ alkyl) group, a C$_1$-C$_6$ alkoxy group, a trifluoromethyl group, a di(C$_1$-C$_6$ alkyl)amino(C$_1$-C$_6$ alkyl) group, an acylamino group of formula —NHCOC$_n$H$_{2n+1}$, with n from 0 to 6, a group —NH—CSC$_n$H$_{2n+1}$ with n from 0 to 6, a terpenyl group, a cyano group, a C$_2$-C$_6$ alkynyl group, a C$_2$-C$_6$ alkynyl group substituted with a C$_1$-C$_6$ alkyl or an aryl group, a hydroxy(C$_1$-C$_6$ alkyl) group, a ($C_1$-$C_6$ acyl) oxy ($C_1$-$C_6$ alkyl) group, a ($C_1$-$C_6$ alkyl) thio group and an arylthio group;
or alternatively $R_1$ and $R_2$ together form a mono- or polycyclic $C_2$-$C_{20}$ alkylene group optionally comprising one or more hetero atoms.

R is chosen from a $C_1$-$C_6$ alkyl group, and their pharmaceutically acceptable salts.

In the foregoing definition, aryl group or aryl fraction of an arylalkyl group denotes an aromatic carbon-based group such as a phenyl or naphthyl group or an aromatic heterocyclic group such as a thienyl of furyl group, it being possible for these groups to bear one or more substituents chosen from halogen atom, a $C_1$-$C_4$ alkyl group, a $C_1$-$C_4$ alkoxy group, a trifluoromethyl group, a nitro group and a hydroxyl group, one more of the following isobenzothiazolone derivative having the structure:

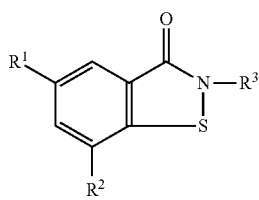

FIG. 24

In this structure at least one of $R^1$ and $R^2$ is preferably nitro, arylazo, substituted arylazo, benzylideneamino or substituted benzylideneamino. When only one of $R^1$ and $R^2$ is so substituted, one of $R^1$ and $R^2$ may be hydrogen. The $R^3$ substituent is selected from alkyl groups in less than about 7 carbon atoms, amino, hydroxyl, alkoxyl, and aryl groups (and functionalized forms thereof).

Preferred species of the isobenzothiazole derivative of the present invention comprise $R^1$ as nitro or arylazo and $R^2$ as hydrogen, for example. Examples include compounds where $R^2$ is hydrogen and $R^1$ is phenylazo; substituted arylazo such as 4-hydroxyphenylazo; 4 nitro-2-methylphenylazo; 2-hydroxy-1-napthylazo; 2-hydroxy-5-methylphenylazo; 2-hydroxy-4-methyl-5-nitrophenylazo; 4-hydroxy-1-napthylazo; 4-hydroxy-3-methyl-1-napthylazo; 4-hydroxy-5-aza-1-napthylazo; 2 amino-1-napthylazo; 1-hydroxy-2-napthylazo; 3-N,Ndimethylaminopropylcarboxyamido-1-hydroxy-4-napthylazo; 1-hydroxy-4-methoxy-2-naphthylazo, 2-hydroxy-3-carboxy-1-naphthylazo; 1-hydroxy-3,6-disulfonato-2-naphthylazo; 2,3-dihydroxy-1-naphthylazo; or 2-hydroxy-3,5-dimenthyl-1-phenylazo. In one particular embodiment $R^1$ is the substituted benzylideneamino, 2,4-dinitrobenzylideneamino and $R^2$ is hydrogen. Additionally $R^1$ is hydrogen and $R^2$ is 2-hydroxy-1-naphthylazo or 4-hydroxy-lphenylazo.

In one aspect, $R^3$ substituents with sufficient polarity to confer aqeuous solubility upon the compound. For example, $R^3$ may be —($CH_2$)n$R^4R^5$ where n is from 2 to 6 and $R^4$ and $R^5$ are simple alkyls or hydrogens. Other possible water solubilizing side chains include 3-carboxypropyl, sulfonatoethyl and polyethyl ethers of the type —$CH_2$($CH_2OCH_2$)$CH_3$ where n is less than 10. Preferred compounds include $R^3$ side chains containing aminoalkyl, carboxyalkyl, omega amino polyethyl ethers and N-haloacetyl derivatives. In a broader sense, for various utilities $R^3$ may be alkyl, aryl, heteroaryl, alkoxy, hydroxyl or amino groups. When including substitutions for solubility or reactivity purposes, $R^3$ may be aminoalkyl, carboxyalkyl, hydroxyalkyl or haloalkyl. The aryl or heteroarl $R^3$ moieties may be substituted, for example as aminoaryl, carboxyaryl or hydroxyaryl, one or more of the following Isobenzothiazolone derivative having the structure:

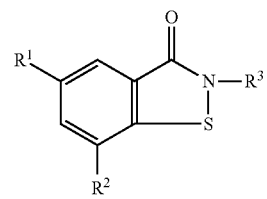

FIG. 25 wherein at least one of $R^1$ and $R^2$ is nitro, arylazo, substituted arylazo, benzylideneamino or substituted benzyfideneamino and one of $R^1$ and $R^2$ may be hydrogen and $R^3$ is a aminoalayl, aminoaryl and aminoheteroaryl, carboxyalkyl, carboxyaryl or carboxyheteroaryl covalently linked to a polymer comprising amino or hydroxy groups. The spacer arm $R^3$ can comprise oligmers or polyethylene-glycol and its derivatives. In one aspect, $R^3$ may be 17-chloracetamido-3,6,9,12,15-pentaoxyheptadecyl where hexaethylene glycol has been chloroacetamidated. When the polymer groups, $Y^1$ and $R^3$ comprises carboxyl groups, the covalent linkage is preferably through an ester bond. When the polymer comprises amino groups, the analog covalent linkage is through an amide bond. The amine bearing polymer, when coupled to $R^3$, may be a polymer such as chitosan, polyalkylamine, aminodextran, polyethyleneimine, polylysine or amitryrene.

The $R^3$ substituents of the present invention may also comprise an alkyl linked to an amine bearing polymer by amine displacement of a halogen from an alpha-haloalkyl or alpha-haloalkylcarbox amido $R^3$ precursor. In the case of aminoalkyl or aminoaryl groups the $R^3$ substituent may also be covalently linked to a polymer such as polyepichlorohydrin, chloromethylpolystyrene, polyvinylalochol or polyvinylpyridine. The $R^3$ substituent of the present invention may generally be an aminoalkyl, hydroxyalkyl, aminoaryl or hydroxyaryl group linked to a polymer comprising carboxyl groups through amide or ester linkages.

When polymers are involved in the $R^3$ structure, the polymer may be one such as polyacrylic acid, polymethacrylic acid, polyilaconic acid, oxidized polyethylene oxide, poly (methylmethacrylate/methacrylic acid), carboxyinethyl cellulose, carboxymethyl agarose or carboxymethyl dextran. When such a carboxyl polymer is involved, the $R^3$ may be aminoalkyl (such as 8 aminohexyl, for example), hydroxyalkyl, aminoaryl or hydroxyaryl linked to the polymer through amide or ester linkages. In such cases, an $R^3$ precursor function may bear an amine or hydroxyl group to be covalently linked to a polymer by reaction with an acid anhydride-bearing polymer or by coupling with a carboxylate bearing polymer through carbodimide induced bond formation.

The $R^3$ substituent or precursor thereto in the compound of the present invention may also be a haloalkyl or carboxylialoalkyl moiety such as chloracetamido. Such a substituent may be readily coupled to an amine bearing polymer by amine displacement of the halogen.

"Aryl," as used herein, is intended to include organic residues derived from aromatic hydrocarbon or aromatic heterocyclic ring systems. Accordingly aryl groups include the unsubstituted ring residues such as phenyl and naphthyl and substituted forms thereof. Heterocyclic or heteroaryl residues may be those comprising one or more heteroatoms (e.g., nitrogen, oxygen, sulphur) in the ring system such as pyridyl, oxazolyl, quinolyl, thiazolyl and substituted forms thereof. "Alkyl" as used herein, is intended to include aliphatic and cyclic organic residues having a carbon at a point of attachment. Accordingly, alkyl groups include unsubstituted hydrocarbon residues of the formula $C_nH_{2n+1}$ and substituted and cyclic forms thereof. Such hydrocarbons are usually of the lower alkyl class which have six carbons or less. It is understood that larger alkyl groups may be used. Alkyl includes substituted residues which are intended to include the hydrocarbon residues bearing one or more, same or different, functional groups as described below.

The alkyl and aryl group previously described may be substituted with functional groups. Such functional groups include essentially all chemical groups which can be introduced synthetically and result in stable compounds. Examples of these functional groups are hydroxyl, halogen (fluoro, chloro, bromo), amino (including alkylamino and dialkylamino), cyano, nitro, carboxy (including carbalkoxy), carbamoyl (including N and N,N alkyl), sulfb, alkoxy, alkyl, aryl, and arylazo,
one or more of the following compounds

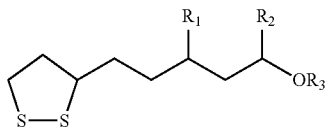

FIG. 26 wherein $R_1$ and $R_2$ are independently (=O) or —OR, where R is H or ($C_1$-$C_4$) alkyl; and $R_3$ is H or ($C_1$-$C_4$) alkyl. Preferably, $R_3$ is H. Preferably $R^1$ and $R_2$ are (=O) or OH,
one or more of the following compounds

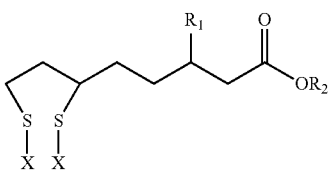

FIG. 27 wherein X is H or both X's represent a direct bond between the two sulphur atoms; $R_1$ is (=O) or —OH; and $R_2$ is H, Na, K or ($C_1$-$C_4$) alkyl.

In particular the compound may be 3-keto lipoic acid, 3-hydroxy lipoic acid, 3-keto dihydrolipoic acid or 3-hydroxy dihydrolipoic acid,
one or more the following
1,2-dithiol-3 thione derivative of a formula shown in FIG. 28

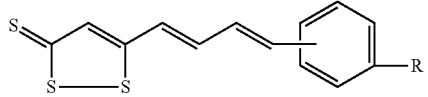

FIG. 28 wherein R denotes hydrogen, halogen, lower alkoxy group, lower alkyl group, amino group, lower alkyl substituted amino group or lower alkoxycarbonyl group.

In the above-described formula FIG. 28, the term "lower" means methyl, ethyl, propyl and butyl, as well as its structural isomers such as isopropyl, isobutyl and tertiarybutyl.

Among the compounds of the formula shown in FIG. 28, preferred compounds include
5-(4-phenyl-1,3-butadienyl)-1,2-dithiol-3-thione,
5-4(4-chlorophenyl)-1,3-butadienyl-1,2-dithiol-3-thione,
5-{4(4-methoxyphenyl)-1,3-butadienyl}-1,2-dithiol-3-thione,
5-{4-(p-toluyl)-1,3-butadienyl}-1,2-dithiol-3-thione,
5-{4-(o-chlorophenyl)-1,3-butadienyl}-1,2-dithiol-3-thione, and
5-{4-(m-(methylpheny)-1,3-butadienyl}-1,2-ffithiol-3-thione.

The following compounds are also included:

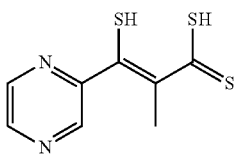

FIG. 29

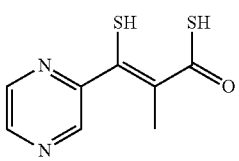

FIG. 30

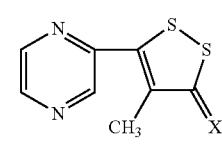

FIG. 31

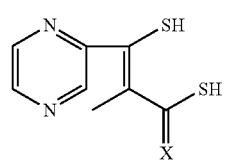

FIG. 31a

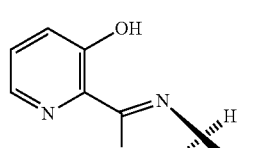

FIG. 32

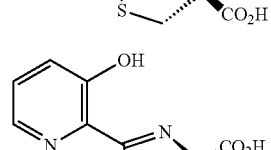

FIG. 33 one or more of the following;
1,2-dithiole of the formula (FIG. 34).

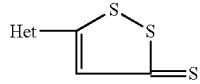

FIG. 34

Wherein Het represents pyrimidin-2-yl, pyrimidin-4-yl, or pyrimidin-5-yl, or a said pyrimidin-2-yl, pyrimidin4-yl or pyrimidin-5-yl substituted by halogen, alkyl of 1 through 4 carbon atoms, alkoxy of 1 through 4 carbon atoms, mecapto, alkylthio of 1 through 4 carbon atoms, or dialkylamino having 1 through 4 carbon atoms in each alkyl, and R represents halogen, alkyl of 1 through 4 carbon atoms, alkyl of 1 through 4 carbon atoms substituted by alkoxycarbonyl having 1 through 4 carbon atoms in the alkoxy, carboxy, alkoxycarbonyl having 1 through 4 carbon atoms in the alkoxy, carbamoyl, N-alkylcarbamoyl having 1 through 4 carbon atoms in the alkyl, or R—CH(OH)— in which R represents hydrogen or alkyl of 1 through 3 carbon atoms.

Without wishing to be bound by theory, the inventor predicts, that the mode of action is derived from $N^6$ isopentenyl adenosine or a derivative or analogue thereof chelating with, or forming a complex with, one or more divalent or trivalent radioactive metal ions, whereby the divalent or trivalent radioactive ions in the subject's cells or tissues are redistributed or sequestered such that the ions are limited in their capacity to participate in unwanted tissue destruction.

In certain embodiments, the divalent or trivalent metal ions are selected from the group comprising, but not limited to: Fe, Cu, Ni, Ca, Mg, Mn, Cd, Pb, Al, Hg, Co, I, Se, Cs, U, Pa, Th, Ra, Ce, and Zn.

In certain embodiments, the cytokinin is a prodrug of a cytokinin provided by the invention, wherein said prodrug is converted into a biologically active or effective compound by metabolism or hydrolysis. In certain further embodiments, said cytokinin compound is further metabolised to form a metabolite, said metabolite mediating the effect of the present invention.

As herein defined, the term "cytokinin" means a compound which is a plant growth substance (plant hormone) which is involved in cell growth and differentiation as well as in other processes. In particular the term encompasses the class of cytokinins termed "adenine cytokines" which include kinetin, zeatin and benzyl adenine. The term further includes "phenylurea cytokinins" such as N, N'-diphenylurea, which although having a differing chemical composition, has a similar biological activity to "adenine cytokinins.

Suitable cytokinin compounds for use in the foregoing aspects of the present invention are provided here as Formula 1 compounds. Examples of suitable Formula 1 compounds are detailed herein in annex 1.

In the embodiments of the invention, wherein the method of this aspect of the invention is performed prophylactically, typically said method is performed prior to the exposure of the subject to an insult, such as a chemical insult, which may result in blood cell number depletion. In certain further embodiments, the insult is a biological insult, a radiation insult or a combination thereof, wherein said insult may induce or cause the progression of blood cell depletion and the ensuing development of a condition such as anaemia, neutropenia or thrombocytopenia.

Where a patient is treated in accordance with the method of this aspect of the present invention, it is preferred that the treatment reduces (1) the severity of pain during vascular or microvascular occlusions, (2) the severity of vascular or microvascular occlusions or (3) the frequency of vascular or microvascular occlusions.

In one embodiment the composition which is administered during the method of the foregoing aspect of the invention comprises at least one cytokinin compound along with at least one pharmaceutically acceptable carrier or diluent.

Further provided is the use of the combined medicament or a pharmaceutical composition comprising the same in the performance of the methods of the present invention for the prophylaxis and/or treatment of a blood cell disorder.

Accordingly, a further aspect of the present invention provides a method for the prevention and/or treatment and/or amelioration of a blood cell deficiency disorder comprising:
providing a therapeutically effective amount of oltipraz, and
administering the same to a subject in need of such treatment.

In certain embodiment, the blood cell disorder is selected from the group comprising, but not limited to; neutropenia, thrombocytopenia or anaemia.

The method of this aspect of the invention has further utility in the treatment of symptoms of neutropenia, thrombocytopenia or anaemia, and accordingly the cytokinin compounds of the invention may be administered to individuals in order to treat such conditions.

In certain embodiments, the neutropenia is postinfectious neutropenia, autoimmune neutropenia, chronic idiopathic neutropenia or a neutropenia resulting from or potentially resulting from a cancer chemotherapy, chemotherapy for an autoimmune disease, an antiviral therapy, direct radiation exposure, secondary radiation exposure through environmental contamination, tissue or solid organ allograft or xenograft rejection or immune suppression therapy in tissue or solid organ transplantation or aging or immunesenescence.

According yet further aspects of the present invention extend to the methods of administrating cytokinin compounds as detailed herein for the treatment of the above-mentioned conditions.

A further aspect of the present invention provides the use of a cytokinin compound in the preparation of a medicament for the prevention and/or treatment and/or amelioration of a blood cell deficiency disorder, such as neutropenia, thrombocytopenia or anaemia in an individual.

In one embodiment, the cytokinin compound is N6 isopentyl adenosine or an analogue or a pharmaceutically acceptable salt thereof. In a further embodiment the cytokinin compound is N6 benzyl adenosine or an analogue or pharmaceutically acceptable salt thereof.

In a further embodiment the cytokinin compounds is a prodrug of the cytokinins that can convert to the biologically active compound by metabolism or hydrolysis.

A yet further aspect of the present invention provides a pharmaceutical composition for the prevention and/or treatment and/or amelioration of a blood cell deficiency disorder, such as neutropenia, thrombocytopenia or anaemia in an individual the composition comprising a cytokinin compound along with at least one pharmaceutically acceptable diluent.

In one embodiment, the cytokinin compound is N6 isopentyl adenosine or an analogue or a pharmaceutically acceptable salt thereof. In a further embodiment the cytokinin compound is N6 benzyl adenosine or an analogue or pharmaceutically acceptable salt thereof.

In a further embodiment the cytokinin compounds is a prodrug of the cytokinins that can convert to the biologically active compound by metabolism or hydrolysis.

The inventor has further identified the surprising utility of oltipraz as well as analogues, derivatives, prodrugs and metabolites thereof in the treatment and/or prophylaxis of blood cell number depletion and conditions such as immune dysregulation and cellular oxidative damage. Such conditions may result from exposure of a subject to radiation, such as gamma radiation.

The compounds of the invention have shown, in irradiated mouse studies, that they have the ability to prevent and treat conditions associated with a depletion in blood cell number such as, but not limited to; neutropenia, thrombocytopenia, and anaemia. Without wishing to be bound by theory, the inventor theorises that said compounds are believed to counteract and neutralize the oxidative damage which radiation causes in living tissue.

In further embodiments, the compound may be 3H-1,2-dithiole-3-thione, anetol trithion and/or sulforaphane, and/or narigin.

In a further embodiment the compound may be selected from the group comprising 5-(4-methoxyphenyl)-3H-1,2-dithiole-3-thione, ADT, ADO, 1,2-dithiole-3-thione, 1,2-dithiolane, 1,3-dithiole-2-thione, and malotilate.

In a further embodiment the compound chelates with, or forms a complex with, one or more divalent or trivalent radioactive metal ions, whereby the divalent or trivalent radioactive ions in the subject's cells or tissues are redistributed or sequestered such that the ions are limited in their capacity to participate in unwanted tissue destruction.

In one embodiment the divalent or trivalent metal ions are selected from Fe, Cu, Ni, Ca, Mg, Mn, Cd, Pb, Al, Hg, Co, I, Se, Cs, U, Pa, Th, Ra, Ce, and Zn ions.

In a further embodiment a compound of Formula 2 enhances the cellular production of phase II detoxification enzymes following their depletion by radiation exposure The phase II detoxification enzymes may be selected from the group consisting of glutathione S transferase, gamma-glutamylcysteine synthetase, glutathione reductase, glutathione peroxidase, epoxide hydrase, AFB-1 aldehyde reductase, glucuronyl reductase; glucose-6-phosphate dehydrogenase, UDP-glucuronyl transferase and AND(P)H: quinone oxidoreductase.

In further embodiments the Formula 2 compound as defined above and selected from the group consisting of: 4-(3,5-diisopropyl-4-hydroxyphenyl)-1,2-dithiole-3-thione; 4-(3,5-di-t-butyl4-hydroxyphenyl)-1,2-dithiole-3-thione; 4-[3,5-bis(I,I-dimethylpropyl)-4-hydroxyphenyl]-1,2-dithiole-3-thione; 4-[3,5bis(I,I-dimethylbutyl)-4-hydroxyphenyl]-1,2-dithiole-3-thione; 4-[3,5-bis(1,1,3,3-tetramethylbutyl)-4-hydroxyphenyl]-1,2-dithiole-3-thion-e; 4-[3,5-bis(I-methylcyclohexyl)-4-hydroxyphenyl]-1,2-dithiole-3-thione; 4-[3,5-bis(I,I-dimethylbenzyl)-4-hydroxyphenyl]-1,2-dithiole-3-thione; 4-(3t-butyl-4-hydroxy-5-isopropylphenyl)-1,2-dithiole-3-thione; 4-(3t-butyl4-hydroxy-5-methylphenyl)-1,2-dithiole-3-thione; 4-[3(1,1-dimethylpropyl)-4-hydroxy-5-isopropylphenyl]-1,2-dithiole-3-thione; 4-[3(1,1-dimethylbenzyl)-4-hydroxy-5-isopropylphenyl]-1,2-dithole-3-thione; 5-benzylthio4-(3,5-di-t-butyl-4-hydroxyphenyl)-1,2-dithiole-3-thion-e; 5-benzylthio-4-[3,5-bis(I,I-dimethylpropyl)-4-hydroxy-phenyl]-1,2-dithi-ole-3-thione; 5-hexylthio-4-(3,5-di-t-butyl-4-hydroxyphenyl)-1,2-dithole-3-thione; 5-hexylthio-4-[3,5-bis(I,I-dimethylbutyl)-4-hydroxy-phenyl]-1,2-d-ithole-3-thione; 5-octadecylthio-4-(3,5-di-t-butyl-4-hydroxyphenyl)-1,2-di-thiole-3-thione; 5-octadecylthio-4-[3,5-bis(I,I-dimethylbenzyl)-4-hydroxyphenyl]-1,2-dithiole-3-thione; 5-allylthio-4-(3,5-di-t-butyl-4-hydroxypheny-l)-1,2-dithiole-3-thione; 5-cyclohexylthio-4-(3,5-di-t-butyl-4-hydroxyphenyl)-1,2-dithiole-3-thione; and 4-(3,5-di-sec-butyl-4-hydroxyphenyl)-1,2-di-thiole-3-thione.

In one embodiment, the method further has utility in the treatment of symptoms of neutropenia, thrombocytopenia or anaemia, and accordingly Oltipraz or derivatives or analogues thereof may be administered to individuals in order to treat such conditions.

In one embodiment, the neutropenia is postinfectious neutropenia, autoimmune neutropenia, chronic idiopathic neutropenia or a neutropenia resulting from or potentially resulting from a cancer chemotherapy, chemotherapy for an autoimmune disease, an antiviral therapy, direct radiation exposure, secondary radiation exposure through environmental contamination, tissue or solid organ allograft or xenograft rejection or immune suppression therapy in tissue or solid organ transplantation or aging or immunesenescence.

According yet further aspects of the present invention extend to the methods of administrating oltipraz as detailed herein for the treatment of the above-mentioned conditions.

A further aspect of the present invention provides the use of oltipraz or a derivative or analogue thereof in the preparation of a medicament for the prevention and/or treatment and/or amelioration of a blood cell deficiency disorder, such as neutropenia, thrombocytopenia or anaemia in an individual.

A yet further aspect of the present invention provides a pharmaceutical composition for the prevention and/or treatment and/or amelioration of a blood cell deficiency disorder, such as neutropenia, thrombocytopenia or anaemia in an individual the composition comprising Oltipraz or a derivative or analogue thereof along with at least one pharmaceutically acceptable diluent.

The present inventor has further identified that administering a therapeutic which is a combination of a cytokinin compound along with oltipraz or a derivative or analogue thereof results in a composition which exhibit a synergistic benefit over the administration of either compound alone in relation to the prevention and/or treatment and/or amelioration of a blood cell deficiency disorder, such as neutropenia, thrombocytopenia or anaemia in an individual.

Accordingly a yet aspect of the provides a method for the prevention and/or treatment and/or amelioration of a blood cell deficiency disorder, such as neutropenia, thrombocytopenia or anaemia in an individual, the method comprising the step of administering to an individual in need of such treatment a therapeutically effective amount of a cytokinin compound along with Itipraz or an analogue or derivative thereof.

In one embodiment, the cytokinin compound is N6 isopentyl adenosine or an analogue or a pharmaceutically acceptable salt thereof. In a further embodiment the cytokinin compound is N6 benzyl adenosine or an analogue or pharmaceutically acceptable salt thereof.

In a further embodiment the cytokinin compounds is a prodrug of the cytokinins that can convert to the biologically active compound by metabolism or hydrolysis.

In one embodiment the individual in need of treatment with the method of this aspect of the invention is a human who has a blood cell deficiency disorder.

Where a patient is treatment in accordance with the method of this aspect of the present invention, it is preferred that the treatment reduces (1) the severity of pain during vascular or microvascular occlusions, (2) the severity of vascular or microvascular occlusions or (3) the frequency of vascular or microvascular occlusions.

A further aspect of the present invention provides the use of a combined medicament, said medicament comprising at least one cytokinin compound and oltipraz in the preparation of a medicament for the prevention and/or treatment and/or amelioration of a blood cell deficiency disorder, such as neutropenia, thrombocytopenia or anaemia in an individual.

In a further embodiment the cytokinin compounds is a prodrug of the cytokinins that can convert to the biologically active compound by metabolism or hydrolysis.

A yet further aspect of the present invention provides a combined pharmaceutical composition for the prevention and/or treatment and/or amelioration of a blood cell deficiency disorder, such as neutropenia, thrombocytopenia or anaemia in an individual the composition comprising a cytokinin compound and oltipraz along with at least one pharmaceutically acceptable diluent.

In one embodiment, the cytokinin compound is N6 isopentyl adenosine or an analogue or a pharmaceutically acceptable salt thereof. In a further embodiment the cytokinin compound is N6 benzyl adenosine or an analogue or pharmaceutically acceptable salt thereof.

In a further embodiment the cytokinin compounds is a prodrug of the cytokinins that can convert to the biologically active compound by metabolism or hydrolysis.

A yet further aspect of the present invention provides a combined medicament comprising Formula 1 and Formula 2 compounds administered to an individual in need of therapy for the prevention and/or treatment and/or amelioration of a blood cell deficiency disorder, such as neutropenia, thrombocytopenia or anaemia. Such compounds may be referred to herein as Formula 3 compounds "F3cs".

In one embodiment the treatment comprises administering said formulation of Formula 1 alone or in combination with Formula 2 compounds in unit doses of 0.01 mg. to 1000 mg/per Kg of bodyweight.

In a further embodiment the compound of Formula 1 and/or Formula 2 are micronized or the compounds are present in a composition that comprises a pharmaceutically acceptable carrier, the carrier optionally selected from phosphatidylcholine, diphosphatidylcholine, vitamin E, a cyclodextrin, magnolol, a microbial preservative, water or a liquid excipient suitable for ophthalmic pharmaceutical formulations, or formulated in a tissue decomposition matrix to allow slow delivery from a polymeric delivery such as with the use of silicone polymers.

It is preferable that the pharmaceutical composition of this aspect of the present invention is provided by combining independently formulated drugs, or by preparing a combination formulation consisting of a mixture of drugs. When the pharmaceutical composition of the present invention is to be used in actuality, unit dosage forms suitable for oral administration are to be formulated and administered according to the conventions of the proper pharmaceutical field. To achieve this, the oral formulation comprises a hard or soft capsule, tablet, powder, etc. The oral formulation, in addition to oltipraz/cytokinin compounds as the pharmacologically active agent, may contain one or more pharmacologically non-active conventional carrier mediums. For example the oral formulation may contain as additives starch, lactose, carboxymethylcellulose, kaolin, and the like excipients; water, gelatin, alcohol, glucose, arabic gum, tragacanth gum and the like binders; starch, dextrine, sodium alginate, and the like disintegrants; talc, stearic acid, magnesium stearate, liquid paraffin, and the like lubricants. Dissolving aids may be further added.

The daily dosage of the present invention depends on various factors such as the patient's degree of liver damage, time of onset of hepatitis, age, health, complications, etc. However, for the average adult, the oltipraz/cytokinin compounds composition is administered once or twice a day for a total daily dosage of 5 to 200 mg, more preferably 25 to 50 mg. However, in patients with severe liver damage or when used as an anti-recurring agent after hepatic carcinectomy, the present invention can depart from the scope of the above pharmaceutical composition and employ even large dosages. Most preferably, one or two unit dosages containing 25 mg of oltipraz and 5 mg of cytokinin compounds are orally administered twice a day.

Modulation of DNA Repair Mechanisms after Radiation Exposure DNA Damage

DNA damage, due to normal metabolic processes inside the cell, occurs at a rate of 50,000 to 500,000 molecular lesions per cell per day.

DNA damage can be subdivided into two main types: endogenous damage such as attack by reactive oxygen radicals produced from normal metabolic by products (spontaneous mutation); (i) exogenous damage caused by external agents such as ultraviolet [UV 200-300 nm] radiation from the sun, (ii) other radiation frequencies, including x-rays and gamma rays, (iii) hydrolysis or thermal disruption (iv) certain plant toxins, (iv) human-made mutagenic chemicals, such as hydrocarbons from cigarette smoke, and (v) cancer chemotherapy and radiotherapy.

Before cell division the replication of damaged DNA can lead to the incorporation of wrong bases opposite damaged ones. After the wrong bases are inherited by daughter cells these become mutated cells (cells that carry mutations), and there is no way back (except through the rare processes of back mutation and gene conversion).

DNA Repair Mechanisms

Cells cannot tolerate DNA damage that compromises the integrity and accessibility of essential information in the genome (but cells remain superficially functional when so-called "non-essential" genes are missing or damaged). Depending on the type of damage inflicted on the DNA's double helical structure, a variety of repair strategies has evolved to restore lost information. As templates for restoration cells use the unmodified complementary strand of the DNA or the sister chromosome. Without access to template information, DNA repair is error-prone (but this can be the standard pathway, e.g. most double strand-breaks in mammalian cells are repaired without template assistance; see below).

Damage to DNA alters the spatial configuration of the helix and such alterations can be detected by the cell. Once damage is localized, specific DNA repair molecules are summoned to, and bind at or near the site of damage, inducing other molecules to bind and form a complex that enables the actual repair to take place. The types of molecules involved and the mechanism of repair that is mobilized depend on the type of DNA damage at stake and whether the cell has entered into a state of senescence the phase of the cell cycle that the cell is in.

Single Strand and Double Strand DNA Damage

When only one of the two strands of a chromosome has a defect, the other strand can be used as a template to guide the correction of the damaged strand. In order to repair damage to one of the two helical domains of DNA, there are numerous mechanisms by which DNA repair can take place. These include direct reversal of damage by various mechanisms that specialize in reversing specific types of damage. Examples include methyl guanine methyl transferase (MGMT) which specifically removes methyl groups from guanine, and photolyase in bacteria, which breaks the chemical bond created by UV light between adjacent thymidine bases. No template strand is required for this form of repair.

Excision repair mechanisms that remove the damaged nucleotide replacing it with an undamaged nucleotide complementary to the nucleotide in the undamaged DNA strand. These include Base excision repair (BER), which repairs damage due to a single nucleotide caused by oxidation, alkylation, hydrolysis, or deamination; Nucleotide excision repair (NER), which repairs damage affecting 2-30 nucleotide-length strands. These include bulky, helix distorting damage, such as thymine dimerization caused by UV light as well as single-strand breaks. A specialized form of NER known as Transcription-Coupled Repair (TCR) deploys high-priority NER repair enzymes to genes that are being actively transcribed; Mismatch repair (MMR), which corrects errors of DNA replication and recombination that result in mis-paired nucleotides following DNA replication.

Double Strand Breaks

A particularly hazardous type of DNA damage to dividing cells is a break to both strands in the double helix. Two mechanisms exist to repair this damage. They are generally known as Non-Homologous End-Joining and recombinational repair, template-assisted repair, or homologous recombination.

Recombinational repair requires the presence of an identical or nearly identical sequence to be used as a template for repair of the break. The enzymatic machinery responsible for this repair process is nearly identical to the machinery responsible for chromosomal crossover in germ cells during meiosis. The recombinational repair mechanism is predominantly used during the phases of the cell cycle when the DNA is replicating or has completed replicating its DNA. This allows a damaged chromosome to be repaired using the newly created sister chromatid as a template, i.e. an identical copy that is moreover orderly paired to the damaged region. Many genes in the human genome are present in multiple copies providing many possible sources of identical sequences. But recombinational repair that relies on these copies as templates for each other is problematic because it leads to chromosomal translocations and other types of chromosomal rearrangements. Non-Homologous End-Joining (NHEJ) rejoins the two ends of the break in absence of a template sequence. However there is often DNA sequence loss during this process and so this repair can be mutagenic. NHEJ can occur at all stages of the cell cycle but in mammalian cells is the main repair mechanism until DNA replication makes it possible for recombinational repair to use the sister chromatid as a template. Since the vast majority of the genome in humans and other multicellular organisms is made up of DNA that contains no genes, the so-called "junk DNA", mutagenic NHEJ is likely to be less harmful than template-assisted repair would be in presence of multiple template sequences, since in the latter case undesirable chromosomal rearrangements are generated. The enzymatic machinery used for NHEJ is also utilized in B-cells to rejoin breaks created by the RAG proteins during VDJ recombination a crucial step in the generation of antibody diversity by the immune system.

Procedures such as chemotherapy and radiotherapy work by overwhelming the capacity of the cell to repair DNA damage and resulting in cell death. Cells that are most rapidly dividing such as cancer cells are preferentially affected. The side effect is that other non-cancerous but similarly rapidly dividing cells such as stem cells in the bone marrow are also affected. Modern cancer treatments attempt to localize the DNA damage to cells and tissues only associated with cancer.

The inventors have surprisingly found that oltipraz can induce DNA repair mechanisms. Such DNA repair can, in particular be mediated following radiation exposure.

Accordingly a yet further aspect of the present invention provides a method of mediating DNA repair in a cell following radiation damage which requires such repair, the method comprising the steps of bringing a therapeutically effective amount of oltipraz or a derivative or analogue thereof into contact with the cell.

In one embodiment the oltipraz derivative or analogue thereof is selected from the group comprising 3H-1,2-dithiole-3-thione, sulforaphane, 5-(4-methoxyphenyl)-3H-1,2-dithiole-3-thione, ADT, ADO, 1,2-dithiole-3-thione, 1,2-dithiolane, 1,3-dithiole-2-thione, and malotilate.

In one embodiment, the cell which requires DNA repair following radiation damage is located in an individual and accordingly this aspect of the invention further extends to a method of treating an individual for DNA repair, the method comprising the steps of administering to the individual a therapeutically effective amount of oltipraz.

In a further embodiment there is provided the use of oltipraz or a derivative or analogue thereof in the preparation of a medicament for the stimulation of cellular DNA repair mechanisms following radiation exposure.

In one embodiment the oltipraz derivative or analogue thereof is selected from the group comprising 3H-1,2-dithiole-3-thione, sulforaphane, 5-(4-methoxyphenyl)-3H-1,2-dithiole-3-thione, ADT, ADO, 1,2-dithiole-3-thione, 1,2-dithiolane, 1,3-dithiole-2-thione, and malotilate.

A yet further aspect of the present invention provides a pharmaceutical composition for mediating DNA repair following radiation exposure comprising oltipraz or a derivative or analogue thereof along with a pharmaceutically acceptable carrier.

In one embodiment the oltipraz derivative or analogue thereof is selected from the group comprising 3H-1,2-dithiole-3-thione, sulforaphane, 5-(4-methoxyphenyl)-3H-1,2-dithiole-3-thione, ADT, ADO, 1,2-dithiole-3-thione, 1,2-dithiolane, 1,3-dithiole-2-thione, and malotilate.

Immunosuppression Caused by Space Flight

The conditions experienced during space flight, such as isolation, stress, containment, microgravity and radiation are all thought to mediate a suppressive effect on the immune system. In particular, radiation can cause damage to human bone marrow stem cells which are the precursor cells for the cells of the immune system.

Human exposure to solar radiation during space travel can amount to up to 3 Gy of proton and gamma radiation. This can result in immunosuppression which can further lead to the reactivation of latent viral infection and malignancy. The immune cells which are particularly susceptible to such solar radiation include; bone marrow stem cells (CD34+ cells), helper T cells (CD4+), cytotoxic T cells (CD8+), B cells (CD19+), monocytes and macrophages (CD19+) and natural killer (NK) cells (CD56+).

The present inventor has identified that the compounds of the present invention have further utility in the treatment and prevention of radiation induced immunosuppression during space travel.

Accordingly a further aspect of the present invention provides a method of treating and or preventing radiation induced immunosuppression, wherein the radiation is derived from solar radiation, particularly proton or gamma radiation, the method comprising administering to an individual in need of such treatment a therapeutically effective amount of at least one of the compounds of the present invention.

Treatment/Therapy

The term 'treatment' is used herein to refer to any regimen that can benefit a human or non-human animal. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

As used herein, the term "therapeutically effective amount" means the amount of a composition which is required to reduce the severity of and/or ameliorate blood cell depletion or at least one condition or symptom which results therefrom.

As used herein, the term "prophylactically effective amount" relates to the amount of a composition which is required to prevent the initial onset, progression or recurrence of blood cell depletion or at least one symptom or condition which results from blood cell depletion by the administration of the compounds of the present invention.

As used herein, the term "subject" refers to an animal, preferably a mammal and in particular a human. In a particular embodiment, the subject is a mammal, in particular a human, who has been, or who is going to be exposed to radiation, for example radiation therapy such as chemotherapy or radiotherapy. The term "subject" is interchangeable with the term "patient" as used herein.

Administration

The products of the invention may be administered alone but will preferably be administered as part of a pharmaceutical composition, which will generally also comprise a suitable pharmaceutical excipient, diluent or carrier which would be selected depending on the intended route of administration.

The products of the invention may be administered to a patient in need of treatment via any suitable route. The precise dose will depend upon a number of factors.

Route of administration may include; parenterally (including subcutaneous, intramuscular, intravenous, by means of, for example a drip patch), some further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebuliser or inhaler, or by an implant.

In preferred embodiments, the composition is administered orally, or is administered to the lungs as an aerosol via oral or nasal inhalation.

For administration via the oral or nasal inhalation routes, preferably the active ingredient will be in a suitable pharmaceutical formulation and may be delivered using a mechanical form including, but not restricted to an inhaler or nebuliser device.

Further, where the oral or nasal inhalation routes are used, administration is by a SPAG (small particulate aerosol generator) may be used.

For intravenous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly(2-hydroxyethyl-methacrylate) or ethylene vinyl acetate (Langer et al, J. Biomed. Mater. Res. 15: 167-277, 1981, and Langer, Chem. Tech. 12:98-105, 1982).

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7th Edition ISBN 0-683305-72-7 the entire disclosures of which is herein incorporated by reference.

Pharmaceutical Compositions

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the radiation damage to be treated, the condition of the individual patient, the site of delivery, the method of administration and other factors known to practitioners.

Prescription of treatment, e.g. decisions on dosage etc, is ultimately within the responsibility and at the discretion of general practitioners, physicians or other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well a two or more different active agents in combination, while references to "a carrier" includes mixtures of two or more carriers as well as a single carrier, and the like.

DETAILED DESCRIPTION OF THE INVENTION

Salts and Solvates

The active compounds disclosed herein can, as noted above, can be prepared in the form of their pharmaceutically acceptable salts. Pharmaceutically acceptable salts are salts that retain the desired biological activity of the parent compound and do not impart undesired toxicological effects. Examples of pharmaceutically acceptable salts are discussed in Berge et al., 1977, "Pharmaceutically Acceptable Salts," J. Pharm. ScL, Vol. 66, pp. 1-19.

The active compounds disclosed may also be prepared in the form of their solvates. The term "solvate" is used herein in the conventional sense to refer to a complex of solute (e.g., active compound, salt of active compound) and solvent. If the solvent is water, the solvate may be conveniently referred to as a hydrate, for example, a hemihydrate, monohydrate, dihydrate, trihydrate, tetrahydrate, and the like.

Prodrugs

The invention further extends to prodrugs of the compounds of the present invention. A prodrug of any of the compounds can be made using well known pharmacological techniques.

Homologues and Analogues

The present invention is further intended to encompass, in addition to the use of the above listed compounds, the use of homologues, derivatives and analogues of such compounds. In this context, homologues are molecules having substantial structural similarities to the above-described compounds and analogues are molecules having substantial biological similarities regardless of structural similarities.

The invention further provides kits for carrying out the therapeutic regimens of the invention. Such kits may comprise, in one or more containers, therapeutically or prophylactically effective amounts of the compositions of the invention in a pharmaceutically acceptable form. Such kits may further include instructions for the use of the compositions of the invention, or for the performance of the methods of the invention, or may provide further information to provide a physician with information appropriate to treating blood cell depletion or conditions resulting therefrom.

Figure 2:
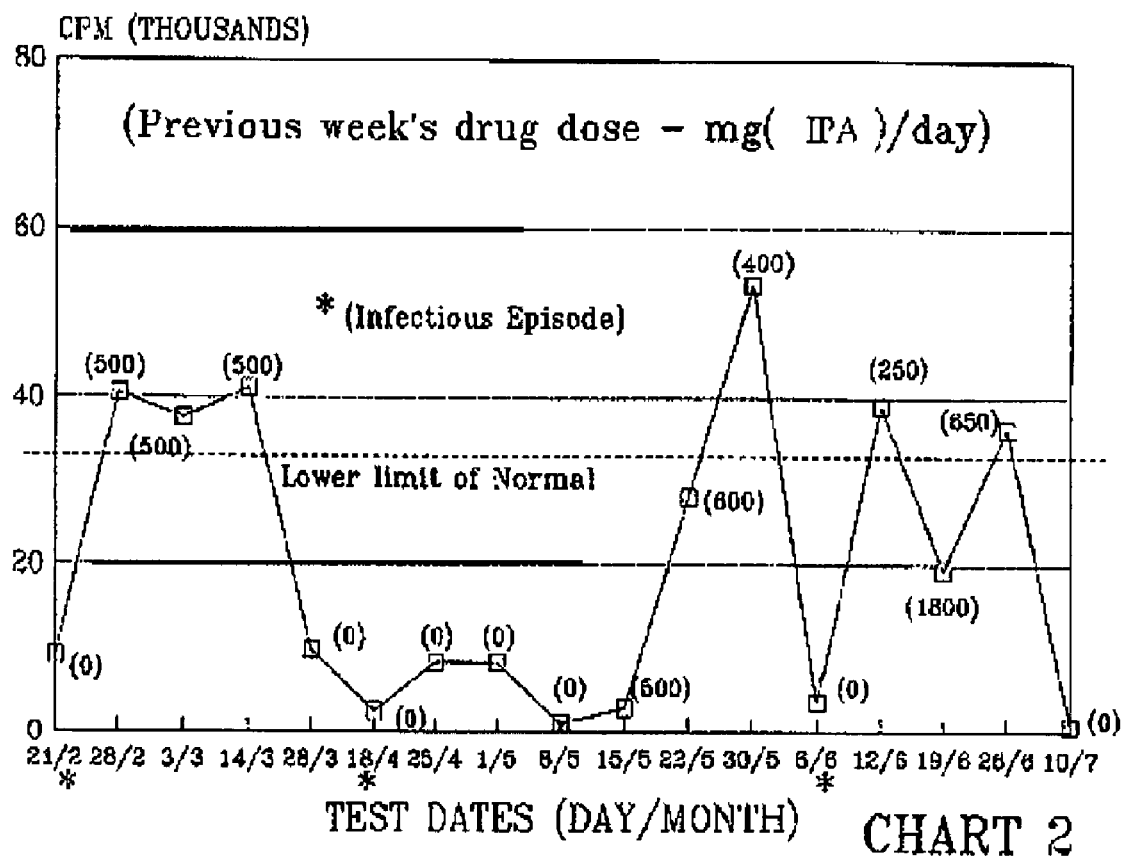

The present invention will now be described with reference to the following examples which are provided for the purpose of illustration and are not intended to be construed as being limiting on the present invention. The present invention will make reference to the following figures, wherein:

FIG. 1 shows a graph illustrating B lymphocyte function following administration of IPA, and FIG. 2 shows a graph illustrating T lymphocyte function following administration of IPA.

EXAMPLES

Example 1

Materials and Methods

Riboflavin, Nitroblue tetrazolium (NBT), reduced glutathione (GSH), S—S' dithiobis (2-nitrobenzoic acid) (DTNB), and 1-chloro-2, 4-dinitrobenzene (CDNB) were obtained from Sisco Research Laboratories Pvt. Ltd, Mumbai, India. Thiobarbituric acid was purchased from Hi-media laboratories, Mumbai, India, 1,1,3,3-tetramethoxy propane was supplied from Sigma-Aldrich USA. All other chemicals and reagents used in this study were of analytical grade. Oltipraz was supplied by the contractor Canopus Corp.

Inbred 4-6 weeks old female Swiss albino mice (20-30 g) were obtained from Small animal breeding station, Kerala Agricultural University, Mannuthy, Thrissur. Animals were kept in well-ventilated cages under standard conditions of temperature, pressure and humidity. The animals were provided with normal mouse chow and water ad libitum. All animal experiments conducted during the present study got prior permission and followed the guidelines of Institutional Animal Ethics Committee (IAEC).

Irradiation

Animals were treated with a single dose of radiation of 700 rads (7Gy). The source of radiation was a 6° Co Theratron-Phoenix teletherapy unit (Atomic Energy Ltd, Canada). Animals were restrained in specially designed, well-ventilated cages without anesthesia and exposed to whole body radiation at a rate of 1.33 Gy/min in a field size of 25×25 cm$^2$ and at a distance of 80 cm from the source.

Determination of effect of oltipraz on haematological parameters of irradiated animals Twenty-four mice were randomly divided into three groups of 8 animals each. Group I was treated as irradiated control served with vehicle. Group II was treated with oltipraz (50 mgs/Kg b wt) ten days prior to irradiation. Group III was administered oltipraz (50 mgs/Kg b. wt) ten days prior to irradiation and continued for another fifteen days after irradiation. All the three groups were irradiated with a single dose of 750 rads. Body weights of all the animals were determined one day prior to irradiation and every third day thereafter. Blood was collected from tail vein into heparinized tubes and the following parameters were analyzed one day before radiation and every third day thereafter. The parameters analyzed were total WBC count (haemocytometer method), differential count (Leishman's staining method) and haemoglobin by Drabkin's method). Determination of effect of oltipraz on bone marrow viability and antioxidant parameters of irradiated animals.

Thirty six animals were divided into four groups of nine animals each. For group 1 to 4 treatment protocol were similar as described above. Group 4 was treated as normal animals without any treatment. On days 5, 10 and 15 after irradiation (750) rads three animals from each group was sacrificed. Blood was collected to heparinized tubes, and plasma was removed and following parameters were assayed in the blood. Activity of the enzyme SOD was measured by NBT reduction method of McCord and Fridovich. CAT activity was estimated by the method of Aebi by measuring the rate of decomposition of hydrogen peroxide at 240 nm. Level of GSH was assayed by the method of Moron et al based on the reaction with DTBN. Assay of GPX followed the method of Hafeman based on the degradation of $H_2O_2$ in the presence of GSH. The method of Habig was followed to assay the activity of GST based on the rate of increase in the conjugate formation between GSH and CDNB.

The femurs of three above animals were dissected out and bone marrow cells were flushed into phosphate buffered saline (pH 7.4) containing 2% foetal calf serum. The cells were washed and bone marrow viability was determined by the method of Sredni. The results were expressed as number of live bone marrow cells ×10(6)/femur.

The liver of the sacrificed animals were excised quickly washed in ice-cold saline and kept at −70° C. till the day of analysis. On the day of analysis 25% homogenate was prepared in tris-HCl buffer (0.1 M, pH 7.4). The homogenate was centrifuged at 12000 rpm for 30 minutes and supernatant was used to determine the tissue lipid peroxide levels (LPO) using the TBA method of Okhawa et al.

Data Analysis

Data was expressed as mean i standard deviation (SD). Significance levels for comparison of differences were determined using Student's t test. The mean of Oltipraz treated group was compared with that of radiation alone treated group. The radiation alone treated group was then further compared with untreated group. The differences between means were considered to be statistically significant if p<−0.001.

Radiation treatment at the dose level used here did not produce a statistically significant reduction in the body-weight of the exposed animals. Initial body weight of animals were 26.27±3.76, 23.92±4.61 and 24.98±3.76 respectively for group I, II and III. On day 6 body weight was reduced to 21.82±3.34, 21.02±4.14 and 21.10±2.51 respectively (p>0.05). Radiation significantly lowered the total leukocyte count in irradiated animals. Administration of oltipraz was found to increase the count. In the initial days after irradiation both group II (oltipraz pre treated group) and group III (oltipraz continuously administered group) showed almost similar number of WBC. But at later days after irradiation, group III showed a significantly elevated WBC as compared with group I (radiation alone treated group) and group II. This indicated that continuous oltipraz administration stimulated the haematopoietic system in a concentration dependent manner.

This observation is further supported by the increased bone marrow viability found in-group III. Bone marrow viability in normal animals was (Group IV) was $16.21 \pm 0.45 \times 10^6$ cells/femur. Bone marrow viability was significantly decreased after irradiation. After the 15th day of post-irradiation group II possessed a value of $6.1 \times 10^6$ cells/femur where as group II and III showed $5.82 \times 106$ and $14.32 \times 10^6$ cells/femur respectively. The haemoglobin levels were significantly reduced after irradiation. On day 6 radiation alone treated group had a hemoglobin level of 10.37±3.19 where as oltipraz continuously administered group had a value of 12.42±2.76. The differential count did not show any significant variation.

The activity of both SOD and CAT, two of the major enzymes involved in the antioxidant defence mechanism were found to be decreased after irradiation The continuous administration of Oltipraz enhanced SOD activity, which showed the maximum value on the 15th day after irradiation and CAT on tenth day after irradiation.

Activity of GPX was also found to be decreased after whole body irradiation. Continuous administration of oltipraz elevated the activity of GPX. On the 15th day after irradiation group I had an activity of 1254.00±116.23 U/L of haemolysate whereas group III showed an activity of 1927.87±136.06 demonstrating that oltipraz administration stimulated GPX activity (p<−0.001). The levels of the major cellular antioxidant GSH increased after oltipraz administration. The levels of GSH were brought down after irradiation. On the 15th day the levels of GSH increased almost three times in oltipraz continuously administered group as compared with radiation alone treated group indicating that oltipraz administration elevated the GSH levels (p<0.001), It could be presumed that an increased level of anti-oxidant enzymes and GSH is a direct consequence of oltipraz administration and could be seen in un-irradiated animals as well. Oltipraz administration also elevated the activity of GST, an enzyme involved in the glutathione mediated detoxification system. On the 15th day group III showed an activity of 2.38±0.25 (nano-moles of CDNB-GSH conjugate formed) (p<−0.01) where as group I had an activity of 1.51±0.37 only. Radiation increased the levels of lipid peroxidation in all the radiation treated animals. On day 15, it was 3.47±0.31 (nano-moles of MDA formed/mg of protein for group I, whereas in-group III it was significantly reduced to a level of 2.12±0.21 (p<−0.001).

Example 2

Patient Case Study

The patient was treated with a Formula 2 compound and blood cell parameters were monitored. The sample size for this experiment was 1, consisting of subject 1. Subject 1 is an immune comprised patient with multiple recurrent infectious bouts requiring hospitalization while in a nearly moribund condition began treatment with the experimental drug Isopentyl adenosine (IPA).

The subject had been hospitalized with avert life-threatening infections. The subject's total white blood cell counts were in the range of 2200-4900 for the three month period preceding hospitalization. A T4/T8 cell ratio of 50/270 (0.22) was observed two months earlier. The patient was hospitalized from depression, exhaustion, bronchial infection, severe diarrhea, severe weight loss and complete loss of appetite and spiked fever. The patient's weight was 98 pounds.

The patient, although initially was very co-operative relative to receiving experimental IPA therapy, for no rational reasons at various times stopped IPA.

Formula 2 Isopentyl Adenosine (IPA) Therapy—Immunological Studies

The subject initially received IPA (see FIGS. 1 and 2). T and B lymphocyte competence as measured by the ability of these cells to proliferate in response to specific stimulating mitogens (PHA for T cells and PWM for B cells) which was monitored on a weekly basis until death. As shown in FIGS. 1 and 2 respectively the subject's T and B lymphocyte competence on was well below normal. Indeed, the competence of both these immune cell populations was less than the 1st percentile of normal donors; that is, greater than 99% of all normal donors historically tested (>1460 normal donors in our laboratory) had responses greater than the patient demonstrated.

A major rapid recovery of both T and B lymphocyte competence was experienced within less than 7 days after initiation of IPA therapy. The levels of competence within 7 days of drug therapy initiation were above the lower limits-of the normal donor's reactivity. This represented a remarkable recovery since patients receiving. Most immune stimulating agents (e.g., BCG, Levamisole) exhibit a slower and less dramatic immune recovery capacity. The subject conscientiously continued to take constant oral doses of IPA.

The subject felt cured and abruptly stopped taking the drug. No one except the subject and his friend were aware of this unilateral decision until several weeks later. Fever and diarrhea in the subject had completely subsided and the patient exhibited a 15 pound weight gain during this time.

As shown in FIGS. 1 and 2, at the time that the patient proclaimed self-cure and thus stopped all IPA medication, his T and B lymphocyte competence again dropped to less than 1% or normal donors' competence.

This was most dramatically observed with T lymphocyte function but was also observed in somewhat lagged fashion with B lymphocyte function. Total WBC counts were in the range of 1650 to 2550 during the period. His peripheral blood showed 50 T4 cells and 220 T8 cells (0.23 ratio).

The patient stopped Formula 2 IPA therapy for a few days. During this time both T and B lymphocyte competence rapidly bottomed out, the patient was hospitalized in for a 7 to 10 day period for severe bronchial infections and fever, diarrhea, anxiety and weight loss.

The subject resumed Formula 2 IPA therapy at recommended dose levels. Minor T lymphocyte competence returned during the following week; B lymphocyte competence continued to decrease. Within two weeks, T lymphocyte competence was again nearly within the normal range. Although B lymphocyte competence was still somewhat depressed, this cell's competence was also improving. Within a month T lymphocyte competence had risen to well within the range of normal donor reactivity, while B lymphocyte competence was somewhat below lower normal limits.

The subject's personal status demonstrated a dramatic improvement; he was periodically dining out with a large appetite, diarrhea had lessened, fever had subsided, he was riding his bicycle daily and partaking in physical activities. The subject again stopped taking medication for a week without the physician's knowledge. T lymphocyte competence again demonstrated a major sudden decrease to less than 1% of normal donors' activity.

The patient again exhibited spiked fever, acute diarrhea and exhaustion. The subject again resumed Formula 2 IPA therapy the following week, for one week, with one-half the recommended dosage taken. The subject's T lymphocyte competence spiked dramatically to above the lower limit of the normal range. B lymphocyte actively demonstrated a slight rise. During the next week the dosage of IPA was greatly (>3×) increased. T lymphocyte competence demonstrated depression suggesting immunotoxicity by IPA; since a 33% decreased dosage the following week resulted in T lymphocyte competence increasing once again.

The patient stopped therapy during the next month, both T and B lymphocyte function fell to nil, as a direct consequence. The patient died approximately two weeks later suffering from acute bronchial infection accompanied with high fever, diarrhea, exhaustion and weight loss.

In conclusion, direct correlations were observed during the period of administration of Formula 2 IPA with quality of life and depressed or elevated T and B lymphocyte function. Enhanced T and B lymphocyte competence correlated well with continued Formula 2 IPA medication; optimum levels of competence appeared to be experienced at optimum IPA dose levels administered. Since competent T and B lymphocyte function is required for combating microbial infections by the host, major infectious bouts correlated with times when competence was most severely compromised. The patient experienced 5 months of life with periods of excellent quality after initiation of Formula 2 IPA therapy at a time when he was terminally moribund. It would appear that the patient would have enjoyed appreciable therapeutic benefits from Formula 2 IPA, if he had conscientiously and continuously received IPA medication. If optimum dose levels had been more clearly established this would have presumably optimized quality and extension of life to a greater extend than was actually observed in this patient.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

Reference to any prior art in this specification is not, and should not be taken as, an acknowledgment or any form of suggestion that this prior art forms part of the common general knowledge in any country.

The invention claimed is:

1. A method for the treatment and/or prophylaxis of blood cell depletion, the method comprising:
   providing a therapeutically effective or prophylactically effective amount of oltipraz or a derivative, analogue, metabolite, prodrug or pharmaceutically acceptable salt thereof; and
   administering same to a subject in need thereof.

2. The method as claimed in claim 1 wherein the blood cell depletion results in at least one condition selected from the group consisting of neutropenia, thrombocytopenia, lymphocytopenia and anaemia.

3. The method as claimed in claim 1 wherein the oltipraz metabolite is metabolite 3.

4. The method as claimed in claim 1 wherein oltipraz or the derivative, analogue, metabolite, prodrug or pharmaceutically acceptable salt thereof is formulated with carboxymethyl cellulose to form a combined medicament.

5. A pharmaceutical composition for use in the treatment of blood cell depletion, the composition comprising oltipraz in the form of metabolite 3 and a pharmaceutically acceptable diluent and/or carrier.

6. The pharmaceutical composition as claimed in claim 5 wherein the composition is formulated along with carboxymethyl cellulose.

7. A method for the treatment and/or prophylaxis of blood cell depletion, the method comprising:
   providing a therapeutically or prophylactically effective amount of at least one cytokinin compound; and
   administering same to a subject in need thereof.

8. The method as claimed in claim 7 wherein the cytokinin compound is $N^6$ isopentenyl adenosine or a derivative, analogue, metabolite, prodrug or pharmaceutically acceptable salt thereof.

9. The method as claimed in claim 8 wherein the $N^6$ isopentenyl adenosine or derivative, analogue, metabolite, prodrug or pharmaceutically acceptable salt thereof is formulated with carboxymethyl cellulose to form a combined medicament.

10. A combined pharmaceutical composition for the prevention and/or treatment and/or amelioration of a blood cell deficiency disorder, the composition comprising a cytokinin compound and a derivative or functionally equivalent analogue of oltipraz along with at least one pharmaceutically acceptable diluent, wherein the analogue or derivative of oltipraz is selected from the group consisting of 3H-1,2-dithiole-3-thione, sulforaphane, 5-(4-methoxyphenyl)-3H-1,2-dithiole-3-thione, ADT, ADO, 1,2-dithiole-3-thione, 1,2-dithiolane, 1,3-dithiole-2-thione and malotilate.

11. The composition as claimed in claim 10 wherein the cytokinin compound is $N^6$ isopentenyl adenosine or an analogue or a pharmaceutically acceptable salt thereof.

12. The composition as claimed in claim 10 wherein the cytokinin compound is $N^6$ benzyl adenosine or an analogue or pharmaceutically acceptable salt thereof.

13. A method of stimulating cellular DNA repair mechanisms in a subject in advance of or following exposure of the subject to radiation, the method comprising the steps of:
   providing a therapeutically or prophylactically effective amount of a composition comprising oltipraz in the form of metabolite 3, and
   administering the composition to the subject.

14. The method as claimed in claim 13 wherein the radiation exposure results from the subject undergoing travel in space.

15. The method as claimed in claim 7 further comprising the step of administering to the subject a therapeutically effective or prophylactically effective amount of oltipraz or a derivative, analogue, metabolite, prodrug or pharmaceutically acceptable salt thereof.

16. A method of treating and/or preventing radiation-induced immunosuppression, the method comprising the step of administering a therapeutically or prophylactically effective amount of $N^6$ isopentenyl adenosine to a subject in need thereof.

17. The composition as claimed in claim 10 wherein the blood cell deficiency disorder is selected from the group consisting of neutropenia, thrombocytopenia and anaemia.

18. A method for the treatment and/or prophylaxis of blood cell depletion, the method comprising:

providing a therapeutically effective or prophylactically effective amount of oltipraz in the form metabolite 3; and administering same to a subject in need thereof.

* * * * *